United States Patent
Ishihara

(10) Patent No.: US 6,622,566 B2
(45) Date of Patent: Sep. 23, 2003

(54) RELEASING/HOOKING FORCE METER OF THE LEADER PIN OF THE MAGNETIC TAPE CARTRIDGE

(75) Inventor: Yusuke Ishihara, Kanagawa (JP)

(73) Assignee: Fuji Photo Film Co., Ltd., Kanagawa (JP)

(*) Notice: Subject to any disclaimer, the term of this patent is extended or adjusted under 35 U.S.C. 154(b) by 0 days.

(21) Appl. No.: 10/139,517

(22) Filed: May 7, 2002

(65) Prior Publication Data

US 2002/0174725 A1 Nov. 28, 2002

(30) Foreign Application Priority Data

May 28, 2001 (JP) ......................................... 2001-158326

(51) Int. Cl.[7] ............................................... G01L 1/00
(52) U.S. Cl. ...................... 73/779; 242/347.1; 360/95; 360/132
(58) Field of Search .................... 73/779, 796, 826, 73/829, 159, 160, 865.8; 360/132, 95; 242/347.1

(56) References Cited

U.S. PATENT DOCUMENTS

| | | | | |
|---|---|---|---|---|
| 5,379,167 A | * | 1/1995 | Robles et al. | 360/95 |
| 6,349,016 B1 | * | 2/2002 | Morita et al. | 360/132 |
| 6,349,892 B2 | * | 2/2002 | Morita et al. | 242/347.1 |
| 6,356,411 B2 | * | 3/2002 | Morita et al. | 360/132 |
| 6,392,836 B1 | * | 5/2002 | Kim | 360/96.5 |
| 6,392,837 B1 | * | 5/2002 | Kim | 360/96.5 |
| 6,435,439 B1 | * | 8/2002 | Ishihara et al. | 242/348.2 |
| 6,437,938 B1 | * | 8/2002 | Wada | 360/95 |
| 6,445,539 B1 | * | 9/2002 | Morita et al. | 360/132 |
| 6,452,745 B1 | * | 9/2002 | Shiga et al. | 360/132 |
| 6,462,905 B1 | * | 10/2002 | Takahashi et al. | 360/132 |
| 6,462,906 B2 | * | 10/2002 | Morita et al. | 360/132 |
| 6,481,658 B1 | * | 11/2002 | Shiga et al. | 242/347 |

* cited by examiner

Primary Examiner—Max Noori
Assistant Examiner—Andre Allen
(74) Attorney, Agent, or Firm—Sughrue Mion, PLLC

(57) ABSTRACT

A releasing/hooking force meter of a leader pin of a magnetic tape cartridge is provided which measures the releasing/hooking force of the leader pin by carrying out a releasing/hooking test. The releasing/hooking force meter includes a first moving part having a gauge head to be engaged with the leader pin; a translation guide for guiding the gauge head in the releasing-and-hooking directions of the leader pin; a second moving part to be connected to the first moving part through a joint; a driving device for achieving the advancing-and-backing movement of the second moving part along the releasing-and-hooking directions of the leader pin; and a compressive tensile load meter for measuring a compressive tensile load added to the joint.

5 Claims, 6 Drawing Sheets

RELEASING/HOOKING FORCE METER OF THE LEADER PIN OF THE MAGNETIC TAPE CARTRIDGE

BACKGROUND OF THE INVENTION

1. Field of the Invention

The present invention relates to the inspection apparatus for checking up a quality of a magnetic tape cartridge, from which a magnetic tape wound on a single reel is drawn out. More specifically, the present invention relates to the inspection apparatus for checking a required force for releasing/hooking the leader pin of the magnetic tape from/to the magnetic tape cartridge.

2. Description of the Related Art

In the magnetic tape cartridge used as the external recording medium for recording the back up data of a computer etc, a single reel, a magnetic tape is to be wound, is rotatably stored within a cartridge case. This cartridge case is composed of an upper half and a lower half, and has a nearly flat square shape. In the occasion of using, the magnetic tape is drawn out from the cartridge case, and is wound up by the reel mounted on a read-write apparatus. The magnetic tape is thus traveled.

An opening for drawing the magnetic tape is formed on the side wall of the cartridge case. This opening is normally covered for preventing the intrusion of dust, and is opened at the time of drawing out the magnetic tape for recording or replaying the data on the magnetic tape using the read-write apparatus.

In the magnetic tape cartridge as represented by LTO (Linear tape open circuit) standard among these conventional magnetic tape cartridges, tip end of a magnetic tape is wound on a thin leader pin and is fixed by nipping with a clip having a C-shape in sectional viewing.

When the magnetic tape is drawn out from the magnetic tape cartridge, the leader pin is caught and pulled. Thus the leader pin should be temporary held at the predetermined position of the magnetic tape cartridge. In the view of standardization, not only the required force for releasing the leader pin from the predetermined position of the magnetic tape cartridge but also the required force for hooking the leader pin to the predetermined position of the magnetic tape cartridge are standardized within the predetermined ranges. In the case of the LTO standard, for example, the required force for releasing/hooking should be within the 0.5 to 1.5N.

For measuring the releasing/hooking force required for releasing/hooking the leader pin from/to the holding position, a releasing/hooking test of the leader pin is carried out using a measurement apparatus, such as a compressive tensile load meter. In that occasion, the measurement is performed by engaging a gauge head, which is connected to the compressive tensile load meter, with the leader pin, and pulling or pushing it, respectively.

At that time, it is ideal that the moving of the gauge head and the moving of the compressive tensile load meter should be carried out along the same single imaginary axis, but, in actually, it cannot be achieved. In the conventional compressive tensile load meter, therefore, the gauge head is connected with the compressive tensile load meter through a floating joint for aligning the position of connecting.

In the conventional floating joint, however, the backlash is established in the orthogonal direction with respect to the moving directions (releasing-and-hooking directions) of the gauge head, and is not established in the moving directions (releasing-and-hooking directions).

The moving directions of the gauge head and the moving directions of the compressive tensile load meter cannot be in agreement accurately even if the position of an axis of them are made in agreement using the floating joint. Thus, the slight friction is arisen in the guide mechanism provided for moving the gauge head and the compressive tensile load meter.

The measurement result is therefore affected by this slight friction, the value much higher than the actual releasing/hooking force is obtained as the measurement result, when the gauge head and the compressive tensile load meter are connected through the floating joint.

SUMMARY OF THE INVENTION

The present invention aim at providing a releasing/hooking force meter, which measures the releasing/hooking force of the leader pin of the magnetic tape cartridge, and which can measure the accurate measurement value even if a slight force, such as a releasing/hooking force of the leader pin. More specifically, the present invention aim at providing a releasing/hooking force meter, which can measure the accurate releasing/hooking force of the leader pin by buffering the position error between the gauge head and the a releasing force meter.

For attaining these objects, there is provided a releasing/hooking force meter of a leader pin of a magnetic tape cartridge, which measures the releasing/hooking force of said leader pin by carrying out the releasing/hooking test, said releasing/hooking force meter comprising; a first moving part having a gauge head to be engaged with said leader pin; a translation guide for guiding said gauge head in the releasing-and-hooking directions of said leader pin; a second moving part to be connected to said first moving part through a joint; a driving means for achieving the advancing-and-backing movement of said second moving part along the releasing-and-hooking directions of said leader pin; and a compressive tensile load meter for measuring a compressive tensile load add to said joint, and is disposed at either of said first moving part or said second moving part; said joint connects said first moving part and said second moving part in the condition that the back lash is established in the parallel and orthogonal directions with respect to the releasing-and-hooking directions, respectively, and said joint is capable of bringing a compressive or tensile load in the releasing-and-hooking directions.

According to this invention, the back lash is established not only in the orthogonal directions with respect to the releasing-and-hooking directions of the leader pin but also in the releasing-and-hooking directions. Thus, the slight displacement in the advancing-and-backing directions of the first and second moving part, respectively, and the displacement caused by the difference of the manufacturing accuracy are buffered by the joint. As a result of this effectiveness, the accurate measurement can be achieved without affected by the unpleasant frictional force.

DESCRIPTION OF THE PREFERRED EMBODIMENTS

The preferred embodiment of the present invention will now be described by referring to the attached drawings.

Figure 6:
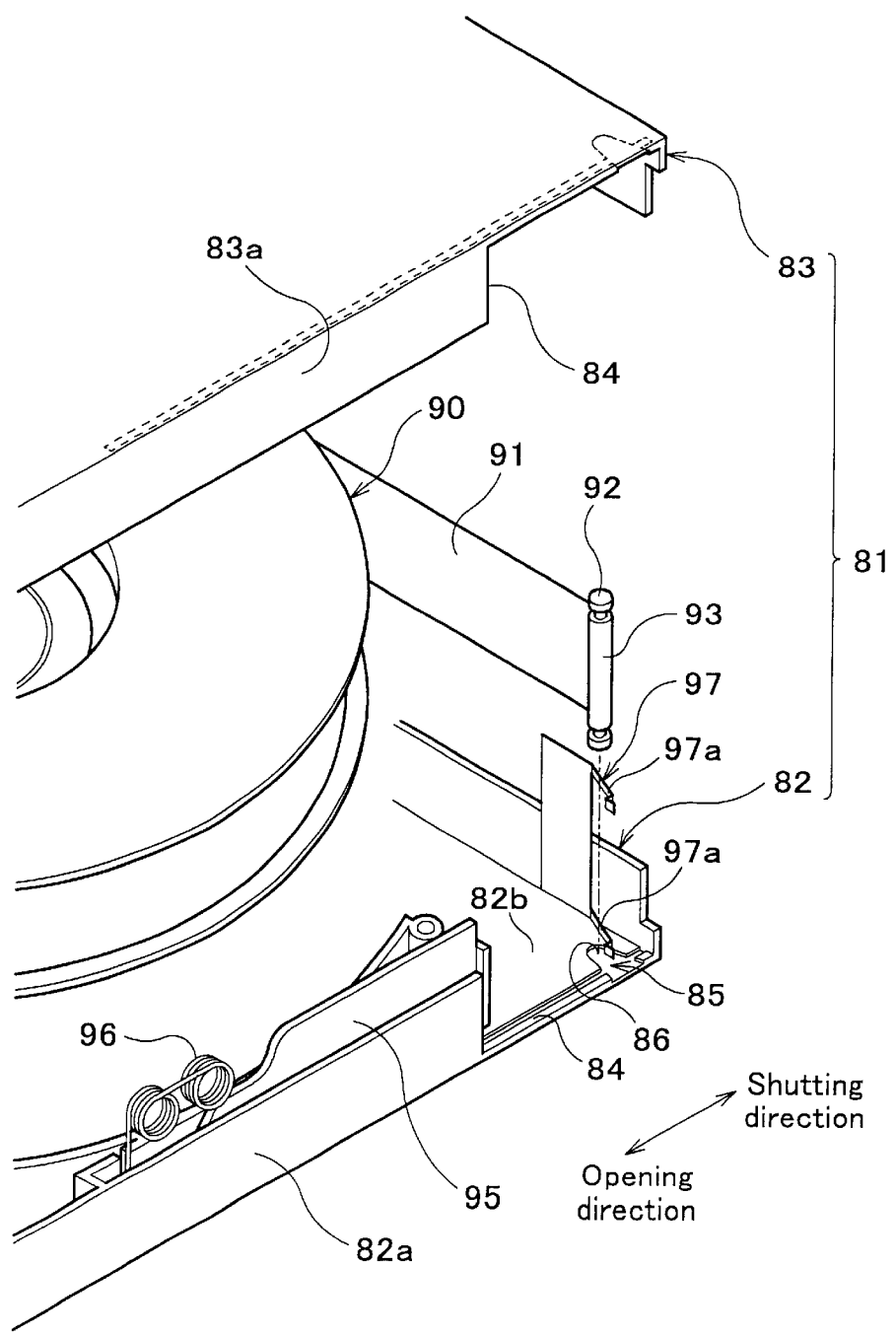
FIG. 6 is an exploded perspective view showing a main part of the magnetic tape cartridge.

First, the explanation about the brief overview of a leader pin and a magnetic tape cartridge will be carried out. FIG. 6 is an exploded perspective view showing one example of a magnetic tape cartridge adopting a LTO standard.

As shown in FIG. 6, a magnetic tape cartridge, a cartridge case 81, is composed of a lower half 82 and an upper half 83, between which a reel 90, a magnetic tape 91 is to be wound, is accommodated. A leader pin 92 is attached at the tip of the magnetic tape 91 by a clip 93.

In the cartridge case 81, an opening 84 for drawing out the magnetic tape 91 is formed ranging over the side wall 82a and the side wall 83a. The shutting-and-opening of the opening 84 is achieved by sliding the slide door 95 along the side wall 82a and the side wall 83a of both half. The slide door 95 is constantly impelled to the shutting direction side by a helical torsion spring 96 having two adjoining coil parts.

A depressed portion 85, having an U-like shape, and open area thereof is facing toward the opening 84 direction, is formed on the bottom face 82b of the lower half 82. When the magnetic tape is stored in the cartridge case 81, the leader pin 92 is approached to the depressed portion 85 from the opening 84 side direction and is caught at the depressed portion 85 by engaging the side end thereof with the depressed portion 85. Thus, the leader pin 92 is held at the depressed portion 85.

A sheet spring 97, at the tip part of which a V-shaped presser 97a is provided, is projected from the side wall to the open area of the depressed portion 85. The presser 97a is established so as to interfere with the leader pin 92 for impelling the leader pin 92 to the depressed portion 85 by the predetermined load. When releasing the leader pin 92 from the depression 85 for drawing out the magnetic tape cartridge from the cartridge case 81, the leader pin 92 is released while deforming the sheet spring 97. As a result of provision of the sheet spring 97 and the depressed portion 85, the holding part 86 for holding the leader pin 9 is established at the semicircle portion (open area) of the depressed part 85.

Figure 1:
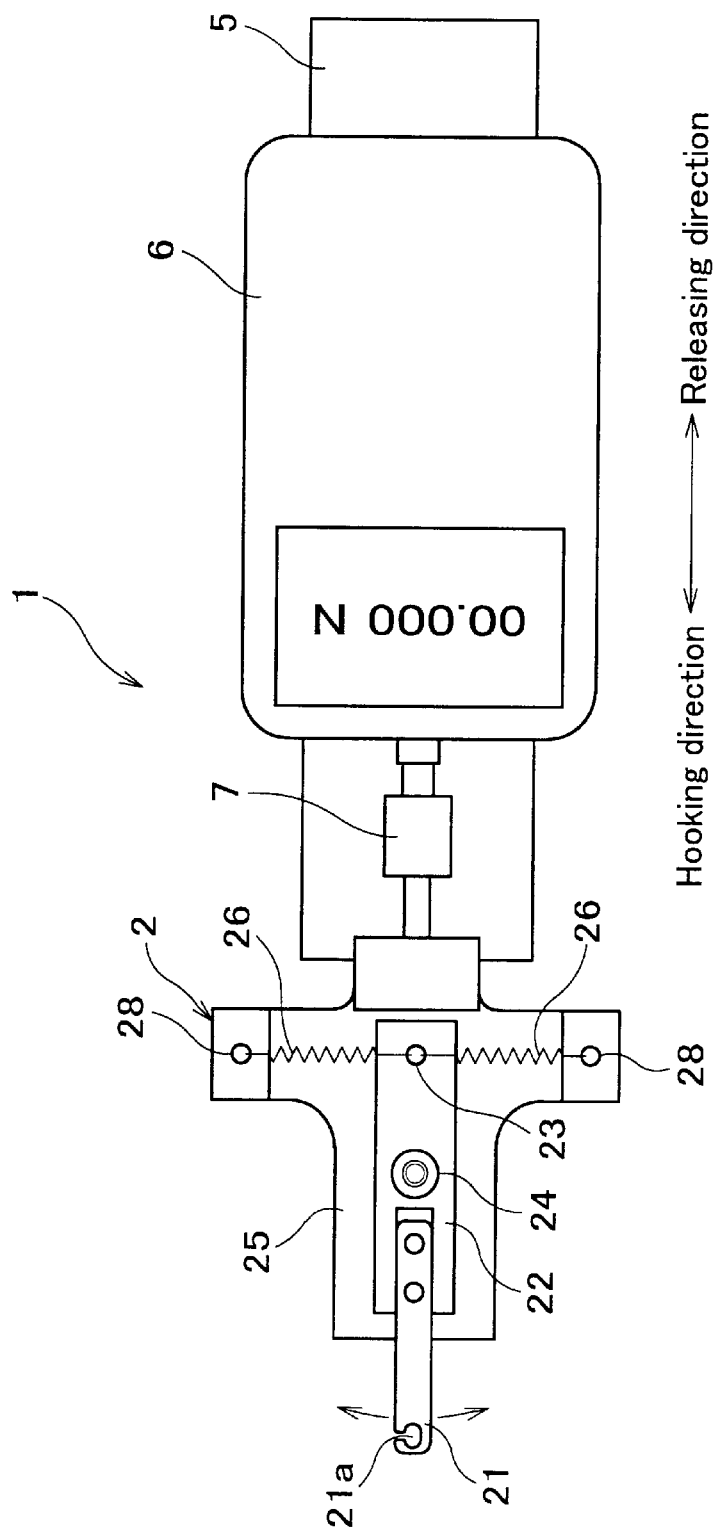
FIG. 1 is a plan view showing a releasing/hooking force meter of the leader pin according to the present invention.
Figure 2:
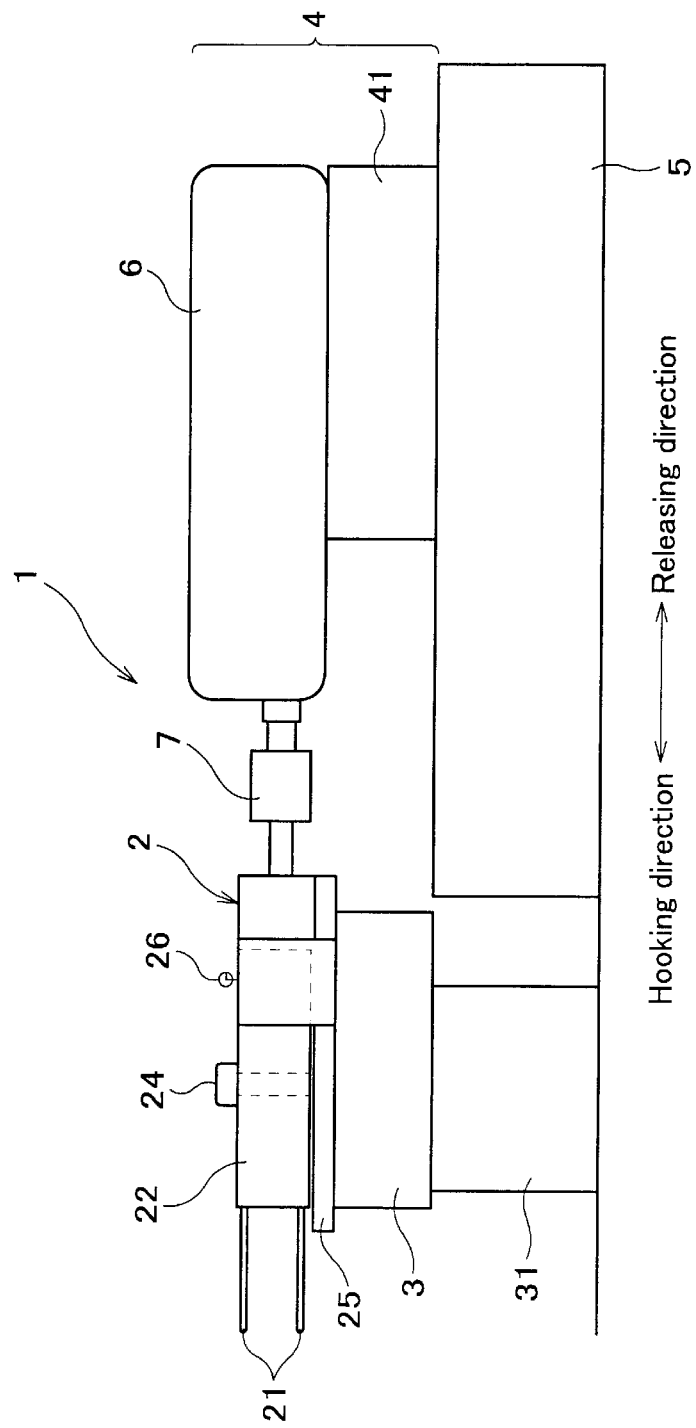
FIG. 2 is a side view showing a releasing/hooking force meter of the leader pin according to the present invention.

Next, the explanation about a releasing/hooking force meter according to the present invention will be carried out. FIG. 1 is a plan view showing a releasing/hooking force meter according to the present invention. FIG. 2 is a side view showing a releasing/hooking force meter according to the present invention.

As shown in FIG. 1 and FIG. 2, a releasing/hooking force meter 1 for measuring a releasing/hooking force of a leader pin, is composed of a first moving part 2, a translation guide 3, a second moving part 4, a compressive tensile load meter 6, and a driving means 5. A first moving part 2 has a gauge head 21 at the tip part thereof, and is guided by the translation guide 3 along the releasing-and-hooking directions, and is connected to the second moving part 4 through a joint 7. A second moving part 4 has the compressive tensile load meter 6 for measuring a load applied to the joint 7, and is made a reciprocation movement along the releasing-and-hooking directions of the leader pin 92 by the driving means 5.

The first moving part 2 is composed of a rotor 22 and a movable table 25. A rotor 22, to which the gauge head of ups-and-downs couple is fixed, is pivotably disposed on the movable table 25 through a supporting shaft 24.

The gauge head 21 made of a spindly plate has an engaging part 21a at the tip part thereof. The engaging part 21a has a hook like shape and is engaged with the leader pin 92 by approaching it from lateral direction in the occasion of using.

As shown in FIG. 2, the gauge head 21 and 21 are fixed at the upside and downside of the rotor 22, respectively, so that they should be in the condition of having separated by the die length of the leader pin 92, and so that they should become parallel each other.

The rotor 22 is supported at the first movable table 25 so that it can pivot centering on the supporting shaft 24. At the vicinity of the rear end part of the rotor 22, a spring hooking hole 23 for hooking the tensile coil spring 26 is perforated form upside to downside of the rotor 22.

The first movable table 25 has a crisscross shape in plan viewing, the both end of the projection part prolonging in the width directions (the ups-and-downs directions in FIG. 1) of the movable table 25 is raised further. A spring hooking hole 28 for hooking one end of the tensile coil spring 26 is provided at the top face of this raised part.

This spring hooking hole 28 and the spring hooking hole 23 is positioned in the same height along the same imaginary line. The tensile coil spring 26 and 26 having same length, respectively, are bridged over the spring hooking hole 28 and the spring hooking hole 23 with same initial tensile force. To be more precise, the bridging of the tensile coil spring 26 is achieved by hooking one end thereof on the spring hooking hole 28, and hooking another end thereof on the spring hooking hole 23.

The two of tensile coil spring 26 are established so as to balance when the hooking hole 23 of the rotor 22 is just in positioned at the mid part between the hooking holes 28 and 28, which are provided at both end of the projection part of the first movable table 25. In this construction, when the gauge head 21 is moved in the right-and-left directions (ups-and-downs directions in FIG. 1), the gauge head 21 is always brought back in the predetermined position by the tensile coil spring 26, and 26.

The translation guide 3 is a guide mechanism capable of moving the first moving table 25 along single imaginary axis with low frictional force using a ball retainer and the like.

The first movable table 25 is placed on the translation guide 3 so that it can move in the releasing-and-hooking directions of the leader pin 92. The height relation between the translation guide 3 and the compressive tensile load meter 6 is adjusted by fixing the translation guide 3 on the height adjusting block 31.

In the present invention, any type of measuring apparatus can be adopted as long as it can measure both compressive load and tensile load with the sufficient accuracy. As an example of such types of apparatus, the apparatus, in which the measurement is achieved electrically using a load cell and a distortion gauge, the apparatus, in which the measurement is achieved mechanically using a spring etc, and the like, can be acceptable.

The second movable table 41 is a movable table capable of achieving a reciprocally movement along single imaginary axis in the releasing-and-hooking directions of the leader pin 92, and is constructed so as to move in the releasing-and-hooking directions by the actuation of the driving means 5. A compressive tensile load meter 6 is fixed on the second movable table 41. This compressive tensile load meter 6 and the second movable table 41 is equivalent to the second moving part The driving means 5 is a mechanism for achieving the reciprocally movement of the second movable table 41, and moves it in the releasing-and-hooking directions of the leader pin 92 along the same single imaginary axis. For example, the uniaxial translatory stage using a ball screw can be adopted.

For achieving the reciprocally movement of the second movable table 41, both of manumotive or automotive manner can be adopted as a driving manner. In the case of manumotive manner, the screw of the uniaxial translatory stage is rotated by the man work, and in the case of automotive manner, the screw is rotated by the motor. In both manner, it is preferable that the movement is achieved without applying excess acceleration for achieving the accurate measurement. In the present embodiment, furthermore, the driving means 5 and the height adjusting block 31 are fixed at the stabled table.

Figure 3:
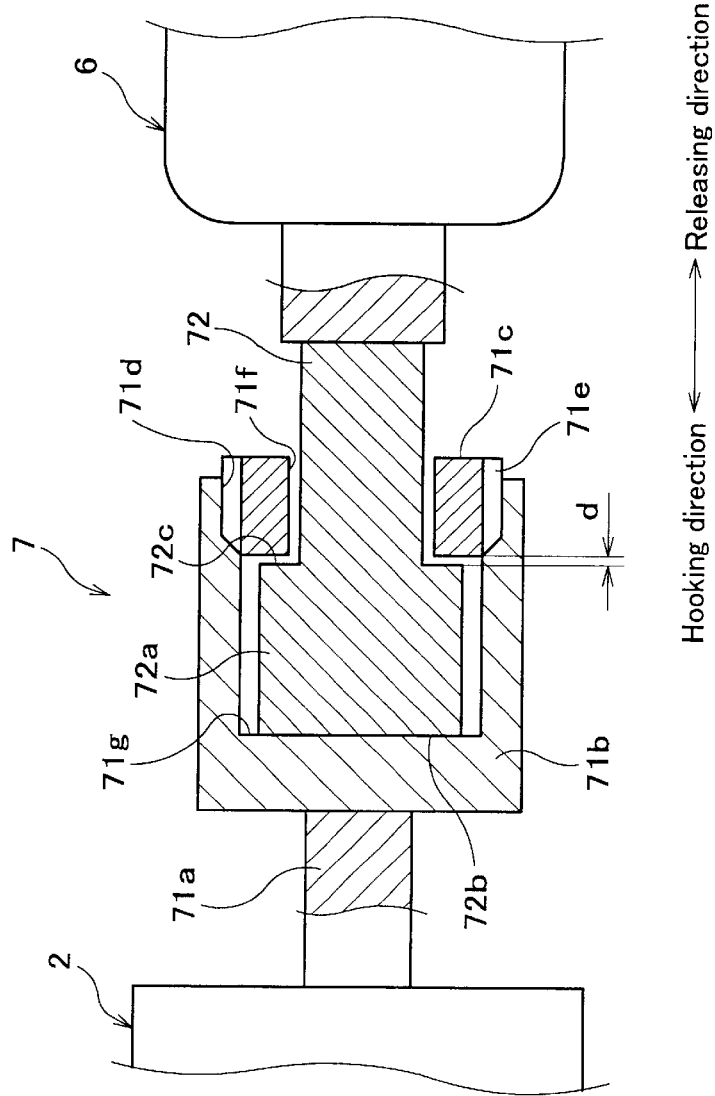
FIG. 3 is an enlarged sectional view showing a joint part of the releasing/hooking force meter of the leader pin according to the present invention.

FIG. 3 is a sectional view showing the connecting condition in the joint 7. As shown in FIG. 3, the joint 7 connects the first moving part 2 with a load measuring part of the compressive tensile load meter 6.

A first rod 71*a* is projected from the first moving part 2, and has a first connecting part 71*b* at the tip part thereof. The first connecting part 71*b* having a bottomed cylindrical shape and is arranged in the condition of having facing the opening thereof toward the compressive tensile road meter 6 side.

A female screw 71*d* is provided at the inner peripheral surface in the opening direction side of the first connecting part 71*b*. A cap 71*c* of ring-like shape has a male screw 71*e* at the periphery thereof, and is screwed into the female screw 71*d*. As an existence of this cap 71*c*, an opening 71*f* having a smaller inside diameter than the first connecting part 71*b* is provided. In other wards, the inside diameter of the opening 71*f* is larger than the diameter of the second rod 72.

A second rod 72 having a stick-like shape is protruded form the compressive tensile load meter 6, and a second connecting part 72 having an one size larger diameter is provided at the end part thereof.

The second connecting part 72*a* is inserted into the first connecting part 71*b* in the condition that the back lash in the diameter directions (the directions orthogonal to the releasing-and-hooking directions) and the back lash d in the axis directions (releasing-and-hooking directions) are established.

When measuring the load required for hooking the leader pin 92 at the holding part 72*a* of the cartridge case 81, the second connecting part 72*a* is advanced in the hooking direction side. At that occasion, since the tip end 72*b* of the second connecting part 72*a* is made into contact with the inner bottom 71*g* of the connecting part 71*b*, the compressive load is transmitted to the compressive tensile load meter 6, and thus, the measurement of the load is achieved.

When measuring the load required for releasing the leader pin 92 from the holding part 86, on the other hand, the second connecting part 72*a* is advanced in the reverse direction. Thus, since the step face 72*c* of the second connecting part 72*a* is made into contact with the cap 71*c*, the tensile load is transmitted to the compressive tensile load meter 6. Then, the measurement of the tensile load is achieved.

The measurement of the releasing/hooking force of the leader pin 92 using releasing/hooking force meter 1 of above described construction is carried out as below.

[The Measurement of the Releasing Force]

First, placing the magnetic tape cartridge in front of the gauge head 21 so that the leader pin 92 might be positioned just in front of the gauge head 21. At that time, the location of them is established so that the releasing direction of the leader pin 92 should be agree with the moving direction of the first moving part 2 and the second moving part 4, respectively.

Next, approaching the gauge head 21 to the leader pin 92 by moving the second moving part 4 and the first moving part 2 using the driving means 5.

At that time, since the engaging part 21*a* of the gauge head 21 is opened sideward, the gauge head 21 is advanced in the condition of having rotated a little around the axis so as not to got stuck with the leader pin 92. Then, making the engaging part 21*a* engaged with the leader pin 92.

Next, backing the gauge head 21 in the other way (in the releasing direction side) by driving the driving means 5 conversely. When the gauge head 21 is backed in the releasing direction, the back lash between the leader pin 92 and the engaging part 21*a* become narrow. When the gauge head 21 is further backed, since the step face 72*c* is made into contact with the cap 71*c* and the tensile load is applied to the leader pin 92, the leader pin 92 is released from the holding condition.

At that time, in the joint 7, the first rod 71*a* and the second rod 72 are engaged while having the back lash in the axis direction and in the diameter direction. To be more precise, as shown in FIG. 3, the second connecting part 72*a* is accommodated in the first connecting part 71*b* in the condition of allowing the displacement in the fore-and-aft directions (releasing-and-hooking directions) and in the diameter directions (in the ups-and-downs directions in FIG. 3).

Therefore, when the moving directions of the first moving part 2 and second moving part 4 are not in certainly agreement, the load (tensile or compression load) is transmitted by making the first rod 71*a* and the second rod 72 in the slanting condition. Thus, the unpleasant force toward side direction is not applied to the driving means 5 and the translation guide 3.

In the releasing/hooking force meter of the leader pin according to the present preferred embodiment, the accurate measurement of the load can be achieved without causing the unpleasant restricting force.

In the releasing/hooking force meter, as described above, the leader pin 92 has been pushed by the sheet spring 97 from it's side direction, and is temporary held at the holding part 72*a*. Thus, the magnetic tape is drawn out in the condition of having displaced to the opposite direction with respect to the side provided with the sheet spring 97, when the magnetic tape is drawn out. In that occasion, since this displacing movement is absorbed by the rotation of the rotor 22, the affection of the unpleasant effect to the measured load is mostly prevented.

Next, releasing the leader pin 92 from the holding part 86 of the cartridge case 81. At that time, the load is transmitted to the compressive tensile load meter 6 from the first moving part 2 through the joint 7, and is measured. After pulling the gauge head 21 until the leader pin 9 is completely drawn out, stopping the driving means 5 and recording the maximum tensile load etc which are measured during the drawn out.

[The Measurement of the Hooking Force]

The measuring manner in the case of hooking the leader pin 92 to the holding part 86 will be explained as below. The explanation will be started from the stage of after achieving the engagement of the gauge head 21 with the leader pin 92.

First, advancing the second rod 72 in the hooking direction side by the actuation of the driving means 5. At that time, since the end face 72b of the second connecting part 72a is made into contact with the inner bottom 71g of the first connecting part 71b, the first moving part 2 is sent forward.

When the first moving part 2 is advanced, the back lash between the engaging part 21a and the leader pin 92 becomes narrow. As a result of further advancing, the load acting as the pushing force, which pushes the leader pin 92 to the holding part 86, is arisen. Then, this load is transmitted to the compressive tensile load meter 6 through the first moving part 2 and the joint 7, and thus the load is measured.

In this occasion, the load is transmitted by making the first rod 71a and the second rod 72 in the slanting condition depending on the displacement in the moving directions of the first moving part 2 and the second moving part 4, as well as the measurement of the load required for releasing the leader pin 92. Thus, the unpleasant force toward side direction is not applied to the driving means 5 and the translation guide 3.

In the releasing/hooking force meter of the leader pin according to the present preferred embodiment, the accurate measurement of the load can be achieved without causing the unpleasant restricting force.

Then, advancing the leader pin 92 by the gauge head 21 until the leader pin 92 is certainly hooked at the holding part 86. When the leader pin 92 is certainly hooked at the holding part 86, stopping the driving means 5, and recording the maximum load etc which are measured until it, and finally finishing the measurement.

As described above, the explanation about the preferred embodiment of the present invention was carried out. The present invention is not limited to this embodiment, and any type of construction can be acceptable as long as the back lash in the orthogonal directions with respect to the releasing-and-hooking directions of the leader pin 92 and the back lash in the releasing-and-hooking directions of the leader pin 92 are established.

In the present embodiment, the end part of one connecting part is formed in the stick-like shape of having a one size larger diameter, and the end part of the another connecting part is formed so as to accommodate the stick-like shaped part. The shape of one connecting part is not restricted to this, for example the shape, such as sphere-like shape, rectangular-like shape, multifaceted shape, and the like, can be adopted. In this case, the shape of the another connecting part should be established so as to surround and accommodate one connecting part of the connecting part with suitable back lash.

Figure 4:
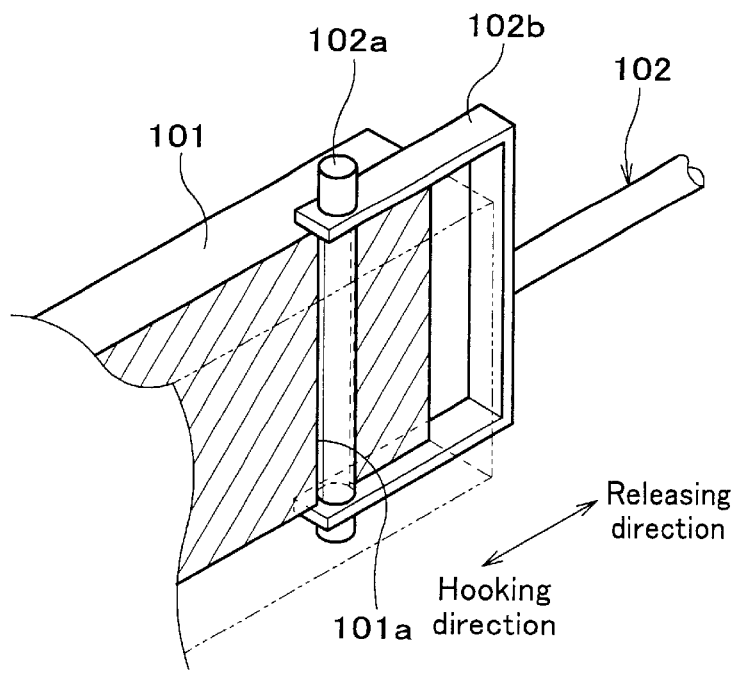
FIG. 4 is a perspective sectional view showing an another embodiment of the joint.

In the present invention, the construction as shown in FIG. 4 can be acceptable. In this construction, one connecting part 101 is a plate having a rectangular shape in sectional viewing, and the through-hole 101a perforated from top face to the bottom face thereof is provided. Another connecting part 102b is composed of a plate member having a horseshoe-shape and a pin 102a for passing through the through-hole 101a. In this construction, both ends part of the pin 102a are fixed by both ends of the horseshoe-shaped part of the plate member, respectively, so that the back lash is established in the axis directions and the orthogonal directions with respect to the pin 102a. In this construction, since the back lash is established not only in the direction orthogonal to the releasing-and-hooking directions of the leader pin 92 but also in the releasing-and-hooking directions of the leader pin 92, the effectiveness same as that of in the first preferred embodiment can be obtained.

Figure 5:
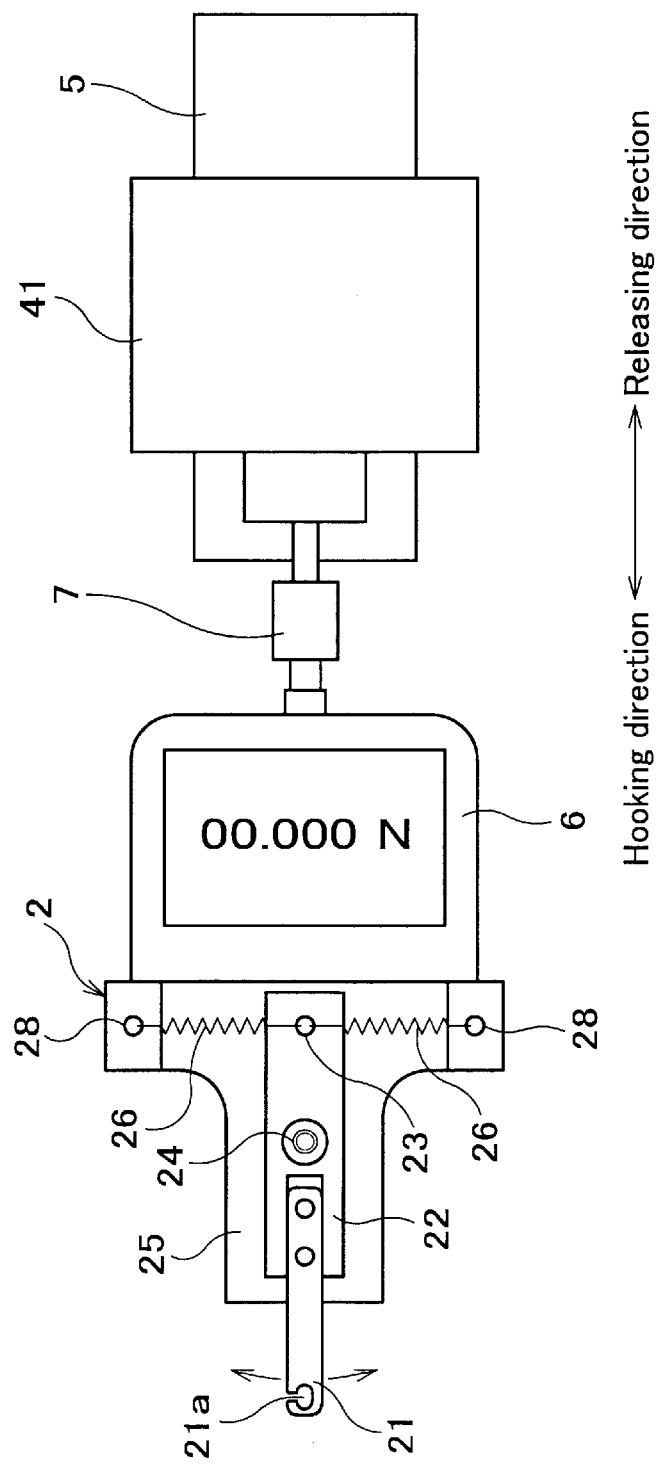
FIG. 5 is a plan view showing an another embodiment of the releasing/hooking force meter of the leader pin.

In the present embodiment, furthermore, the compressive tensile load meter 6 is disposed on the second moving part 4, the formation manner of the tensile load meter 6 is not restricted to this. For example, the manner, in which the compressive tensile load meter 6 is disposed on the first moving part 2, can be acceptable. The releasing/hooking force meter having this construction is shown in FIG. 5. In this FIG. 5, only the arrangement of each parts are differing form that of in the first preferred embodiment, the symbols indicating each parts are same as used in the first preferred embodiment.

As shown in FIG. 5, in this construction, the compressive tensile load meter 6 is disposed in the turned condition, and is connected to the second movable table 41 through the joint 7.

As described above, according to the present invention, since each position and direction error among the relations between the leader pin, the translation guide, the first moving part, the second moving part are buffered by the rotation of the joint. The accurate measurement of the load can be achieved without affected by the unpleasant load arose from the restriction force.

What is claimed is:

1. A releasing/hooking force meter of a leader pin of a magnetic tape cartridge, which measures the releasing/hooking force of said leader pin by carrying out the releasing/hooking test, said releasing/hooking force meter of a leader pin of a magnetic tape cartridge comprising;

a first moving part having a gauge head to be engaged with said leader pin;

a translation guide for guiding said gauge head in the releasing-and-hooking directions of said leader pin;

a second moving part to be connected to said first moving part through a joint;

a driving means for achieving the advancing-and-backing movement of said second moving part along the releasing-and-hooking directions of said leader pin; and a compressive tensile load meter for measuring a compressive tensile load add to said joint, and is disposed at either of said first moving part or said second moving part;

said joint connects said first moving part and said second moving part in the condition that the back lash is established in the parallel and orthogonal directions with respect to the releasing-and-hooking directions, respectively, and said joint is capable of bringing a compressive or tensile load in the releasing-and-hooking directions.

2. A releasing/hooking force meter of a leader pin of a magnetic tape cartridge according to claim 1, wherein said joint is composed of a first rod projected from said first moving part and a second rod projected from said second moving part, said first rod and said second rod are connected together in the condition that the back lash is established in the parallel and orthogonal directions with respect to the releasing-and-hooking directions, respectively, and said first moving part and said second moving part are connected through said first rod and said second rod.

3. A releasing/hooking force meter of a leader pin of a magnetic tape cartridge according to claim 2, further comprising;

a first connecting part having a bottomed cylindrical shape, and said first connecting part is provided at the tip of said first rod in the condition of having facing an opening thereof toward said second rod side;

a second connecting part having an one size larger diameter than said second rod, and said second connecting part is provided at the end part in the first rod side of said second rod, and is inserted into said opening; and a cap having an opening of larger diameter than the diameter of said second rod, and is fixed at the tip end in the second rod side of said first connecting part so as to prevent the disengaging of said second connecting part from said first connecting part.

4. A releasing/hooking force meter of a leader pin of a magnetic tape cartridge according to claim 2, wherein said first rod has a through hole into which a pin is put through, and is connected to said second rod by supporting said pin at a plate member of horseshoe-shape provided on said second rod.

5. A releasing/hooking force meter of a leader pin of a magnetic tape cartridge, which measures the releasing/hooking force of said leader pin by carrying out the releasing/hooking test, said releasing/hooking force meter of a leader pin of a magnetic tape cartridge comprising;

a first moving part having a gauge head to be engaged with said leader pin;

a translation guide for guiding said gauge head in the releasing-and-hooking directions of said leader pin;

a second moving part to be connected to said first moving part through a joint and moves said first moving part in the releasing-and-hooking directions;

a driving means for achieving the advancing-and-backing movement of said second moving part along the releasing-and-hooking directions of said leader pin; and a compressive tensile load meter for measuring a compressive tensile load add to said joint, and is disposed at either of said first moving part or said second moving part;

said joint connects said first moving part and said second moving part in the condition that the back lash is established in the parallel and orthogonal directions with respect to the releasing-and-hooking directions, respectively, thereby, said first moving part and said second moving part are moved in the advancing-and-backing directions along the same imaginary single axis, respectively.

* * * * *